Figure 1:
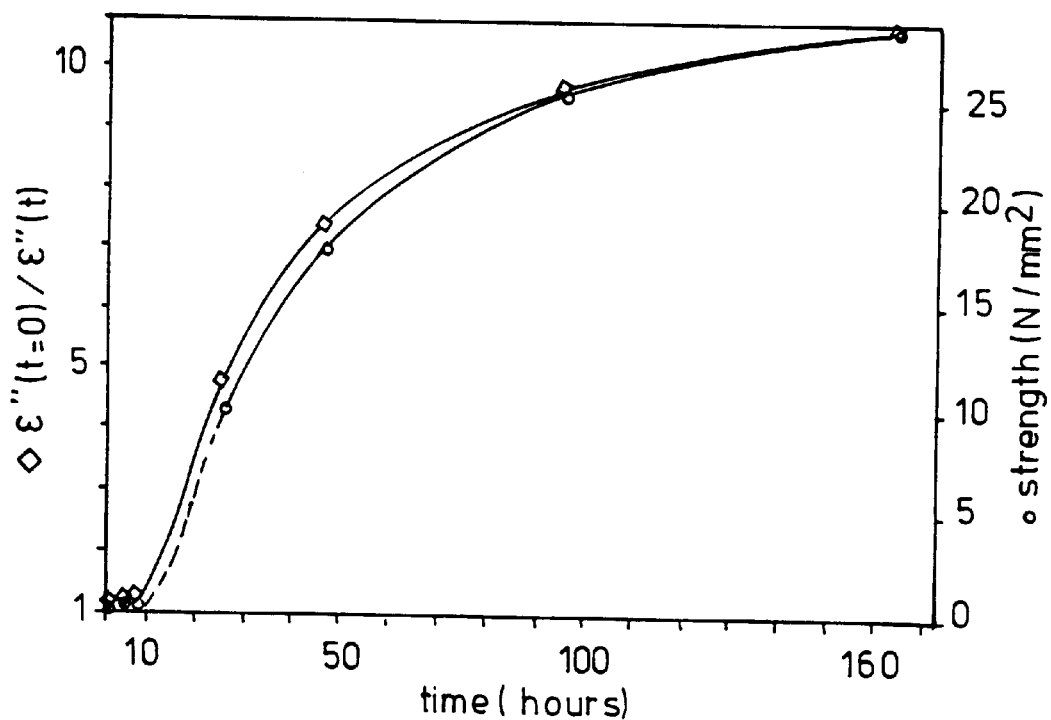

United States Patent [19]
Hilhorst et al.

[11] Patent Number: 6,023,170
[45] Date of Patent: Feb. 8, 2000

[54] METHOD FOR DETERMINING THE DEGREE OF HARDENING OF A MATERIAL

[75] Inventors: Maximus Andreas Hilhorst, Bennekom; Willem Herman Stenfert Kroese, Rotterdam, both of Netherlands

[73] Assignee: Instituut voor Milieu- en Agritechniek, Wageningen, Netherlands

[21] Appl. No.: 08/973,704

[22] PCT Filed: Jun. 7, 1996

[86] PCT No.: PCT/NL96/00228

§ 371 Date: Dec. 8, 1997

§ 102(e) Date: Dec. 8, 1997

[87] PCT Pub. No.: WO96/42014

PCT Pub. Date: Dec. 27, 1996

[30] Foreign Application Priority Data

Jun. 8, 1995 [NL] Netherlands ............................ 1000525

[51] Int. Cl.[7] ................................................ G01N 27/22
[52] U.S. Cl. ........................ 324/689; 324/650; 324/687
[58] Field of Search ................................. 324/687, 689, 324/664, 663, 693, 705, 713, 690, 650

[56] References Cited

U.S. PATENT DOCUMENTS

| | | | |
|---|---|---|---|
| 3,278,843 | 10/1966 | Deming | 324/687 |
| 3,723,865 | 3/1973 | Batey | 324/687 |
| 4,120,166 | 10/1978 | Brooks | 324/696 |
| 4,399,100 | 8/1983 | Zsolnay et al. | |
| 4,423,371 | 12/1983 | Senturia | 324/687 |
| 4,524,319 | 6/1985 | Eberling | 324/693 |
| 4,723,908 | 2/1988 | Kranbuehl | 324/687 |

FOREIGN PATENT DOCUMENTS

| | | |
|---|---|---|
| 2 484 092 | 12/1981 | France . |
| 2 645 275 | 10/1990 | France . |
| 742 784 | 6/1980 | U.S.S.R. . |

OTHER PUBLICATIONS

J. G. Wilson, et al., "Variations in the Electrical Properties of Concrete with Change in Frequency", *IEE Proceedings*, vol. 137, Pt. A, No. 5, Sep. 1990, pp. 246–254.

M.A. Bari, "Comment on Dynamic dielectric analysis during early-stage hydration of ordinary Portland cement", *Journal of Physics D; Applied Physics*, vol. 23, No. 2, Feb. 1990, pp. 234–236.

*Primary Examiner*—Josie Ballato
*Assistant Examiner*—Jose M. Solis
*Attorney, Agent, or Firm*—Young & Thompson

[57] ABSTRACT

A method for determining the degree of hardening of a hardenable material determines the complex electrical permittivity. The $\epsilon''(t=0)/\epsilon''(t)$ ratio, where $\epsilon''(t)$ is the imaginary part of the complex electrical permittivity $\epsilon'(t) - j\epsilon''(t)$, is determined as a measure of the strength of the material at an instant in time t. The $\epsilon'_{max}/\epsilon'(t)$ ratio of the real part of the complex permittivity can also be determined as a measure of the strength. These ratios are similar in shape to the curve of the strengths of the hardenable material with time.

14 Claims, 2 Drawing Sheets

METHOD FOR DETERMINING THE DEGREE OF HARDENING OF A MATERIAL

The invention relates to a method and apparatus for determining the degree of hardening of hardenable materials, in particular materials which harden as a result of water binding, such as concrete, plaster or cement, in which method the complex electrical permittivity of the material is determined at various instants in time.

Such a method is known from the JOURNAL OF PHYSICS D APPLIED PHYSICS., vol. 23, no. 2, Feb. 14, 1990, pages 234–236, XP000099844 M. A. BARI: "COMMENT ON 'DYNAMIC DIELECTRIC ANALYSIS DURING EARLY-STAGE HYDRATION OF ORDINARY PORTLAND CEMENT'". In this document the frequency dependence of the imaginary part and the real part of the capacitance of a sample block of hardening cement is given after 24 hours, 10 days and 50 days of dehydration. No indication is given how the degree of hardening of the concrete can be determined from the observed change in these parameters.

Various other methods have been proposed for determining the degree of hardening. The development of the compressive strength, the ageing or the degree of hydration of hardening, setting or curing materials, in particular materials which become hard as a result of water binding, such as hardening stone-like materials such as concrete, cement and plaster. The development of compressive strength, the ageing or the degree of hydration is a measure of the hardening. The most widely known method is to monitor the development of heat during hardening. The development of heat appears to be linked to the extent of water binding, or hydration. However, said method suffers from some disadvantages. One of the most important disadvantages is that the development of heat has to be followed in a conditioned space so that the necessary measurements have to be carried out on one or more test samples in order to predict the degree of hardening of the actual structure on the basis of said measurements. The temperature of the actual structure may, however, differ appreciably from that in the laboratory. In addition, the measurement of the development of heat is inaccurate and susceptible to errors because of the dependence on various parameters.

IEEE PROCEEDINGS—A PHYSICAL SCIENCE, MEASUREMENT & INSTRUMENTATION, MANAGEMENT & EDUCATION, part 137, No. Sep. 5, 1990, STEVENAGE GB, pages 246–254, XP000150889, J. G. WILSON ET AL.: "VARIATIONS IN THE ELECTRICAL PROPERTIES OF CONCRETE WITH CHANGE IN FREQUENCY" describes how the dielectric constant (or the electrical permittivity) and the conductivity alters for concrete during hardening over a period of not more than 1 day. Again no indication is given of how the degree of hardening of the concrete can be determined reliably and accurately from the observed change in said parameters.

The object of the present invention is to provide a more accurate method for determining the degree of hardening of a material. Moreover, the subject of the invention is a more reliable method of this type. The object of the invention is also to provide a method with which the degree of hardening of the material can be measured accurately and reliably, without the need for separate test samples, directly on the structure itself, preferably in a particularly simple and not very time-consuming manner.

For this purpose, the method according to the present invention is characterized in that the ratio $\epsilon''(t=0)/\epsilon''(t)$ of the imaginary part, $\epsilon''(t)$, of the complex electrical permittivity, $\epsilon'(t)-j\epsilon''(t)$, at a reference instant in time $t=0$ and at an instant in time $t$ and/or the ratio $\epsilon'max/\epsilon'(t)$ of the maximum value of the real part of the complex electrical permittivity, $\epsilon'max$, over the time interval $t=0$ to $t$ and the real part of the complex electrical permittivity, $\epsilon'(t)$, at the instant in time $t$, the time $t$ occuring after the time at which $\epsilon'max$ has occurred, are determined as a measure of the strength of the material at an instant in time $t$.

The dielectric behaviour of a material such as concrete can be described by the complex dielectric constant, also referred to as the complex electrical permittivity. The complex permittivity $\epsilon$ can be expressed as:

$$\epsilon = \epsilon' - j\epsilon''.$$

In this equation, the real part of the permittivity, $\epsilon'$, is a measure of the polarizability of various material constituents, including the water, which is in some cases bound. The imaginary part of the permittivity, $\epsilon''$, is a measure of the absorption of energy. The ionic conductivity contributes to $\epsilon''$. The two components $\epsilon'$ and $\epsilon''$ of the permittivity are measurable, respectively, as the capacitance C (in farads) and the conductivity G (in $Sm^{-1}$) of a capacitor having the hardenable material as dielectric between the electrodes.

The reorientation of a polarizable particle such as water in an alternating electric field requires some time. For increasing frequency, the particles or molecules are too slow to be able to follow the rapidly alternating field. This slowness is influenced, inter alia, by the degree to which the particle or the molecule is bound to its environment. For higher frequencies, $\epsilon'$ then decreases. At higher frequencies, the energy supplied is absorbed, as a result of which the dielectric losses, of which $\epsilon''$ is a measure, increase. For frequencies lower than those at which the most important absorptions take place, $\epsilon''$ is dominated by the ionic conductivity.

As the forces which bind the water molecule to its environment in the hardenable material increase during its ageing, the strength of the material in newtons per $m^2$ can be determined from the real part $\epsilon'$ of the complex electrical permittivity or from the imaginary part $\epsilon''$. Surprisingly, it has been found that, apart from a scaling factor, the curve of $\epsilon''(t=0)/\epsilon''(t)$ against time is to a high degree similar in shape to the curve of the compressive strength of the hardenable material in newtons per $m^2$. The hardening process of the hardenable material can be followed reliably by determining $\epsilon''(t=0)/\epsilon''(t)$ at regular intervals, for example over a period of, for example, a few days to a few weeks. The ratio is insensitive to disturbances in the electrode/dielectric configuration during the measurement.

It has also been found, surprisingly, that the ratio $\epsilon'max/\epsilon'(t)$ correlates very well with the strength of the hardenable material after a hardening period of approximately one day.

Advantageously, the imaginary part, $\epsilon''(t)$, of the complex electrical permittivity can be determined by placing at least two electrodes in or near the hardenable material, applying an alternating current across the electrodes, measuring the alternating voltage across the electrodes, determining the complex impedance $Z^*$, where $$Z^* = \frac{1}{G + j\omega C},$$

where G is the conductivity of the hardenable material in S/m and C is the capacitance in F, and determining $\epsilon''(t)$ via the relationship: $G(t)=k\epsilon''(t)\epsilon_0 \cdot \omega$ and/or determining $\epsilon'(t)$ via the relationship: $C(t)=k\epsilon'(t)\epsilon_0$, where k is a constant.

By placing two electrodes in the hardenable material, in which arrangement the electrodes may, for example, be cylindrical with a length of, for example, 3 cm and a diameter of 1 cm and placed at a mutual spacing of 2 cm, a capacitor is formed with the electrodes as capacitor plates and the hardenable material in between as dielectric. The complex impedance can be determined by measuring the alternating voltage. Said complex impedance is formed by the conductivity G (in $Sm^{-1}$, where $S=Q^{-1}$), from which the imaginary part $\in"(t)$ of the complex electrical permittivity can be determined, and the capacitance C from which the real part $\in'(t)$ of the complex electrical permittivity can be determined. In this connection, the constant k is a geometry factor which depends on the shape and mutual positioning of the electrodes. As a result of setting up the electrodes and measuring the complex impedance with them, the strength of the hardenable material can be determined very simply and reliably in situ without complex equipment being necessary.

Preferably, the strength of the material is determined over a time of between 1 day and 100 days, preferably of between 1 day and 30 days. The frequency used can be between 0 and 17 GHz and is preferably between 15 and 50 MHz. It has been found that, at frequencies below 20 MHz, interfering effects may occur, for example, as a consequence of electrode polarization. Although a relationship between the complex permittivity and the compressive strength is found at higher frequencies, for example above 100 MHz, it is less sensitive and less easy to measure.

As a measure of the strength of the hardenable material, $r \cdot \in"(t=0)/\in"(t)$ preferably is determined, where r is a scaling factor which depends on the composition of the hardenable material. To determine r, a calibration measurement is made prior to the measurement. It is also possible to determine r by determining the maximum value of the real part of the complex electrical permittivity, $\in'max$. which will occur within approximately 1 day after the start of hardening of the hardenable material. The strength can then be calculated from the ratio of $\in'max$ and $\in'(t)$. The scaling factor r can be calculated with this calculated strength. The strength curve can then furthermore be determined using the relationship $r \cdot \in"(t=0)/\in"(t)$. The scaling factor r can furthermore be determined from the fact that, for $\in'max(t)$, the compressive strength appears to be 10.5 $N/mm^2$.

A device for carrying out the method according to the invention comprises an alternating-current source for supplying an alternating current via a supply lead to a supply terminal of the electrodes. Via a branching lead, the alternating current of the current source is also supplied via a switch to a phase-rotating component, such as, for example, a capacitor, or to a non-phase-rotating component, such as a resistor. The voltage which is generated across the electrodes of the measuring arrangement with the hardenable material in between as dielectric and the voltage which is generated across the phase-rotating component or the non-phase-rotating component on the branching lead are multiplied by one another in a multiplier. The output voltage of the multiplier comprises an alternating-voltage component and a direct-voltage component. The alternating voltage is removed by a low-pass filter. If the current in the branching lead is fed via the non-phase-rotating component to the multiplier, the direct current is a measure of the capacitance, C, and if a phase rotation has taken place, the direct current is a measure of the conductivity, G. These values are fed via an analogue/digital converter to a computer in which the real part and/or the complex part of the complex electrical permittivity are determined from the conductivity and the capacitance and a measure of the strength is calculated. With the aid of a time control unit, a number of measurements are made, for example every hour for a number of days, for example seven days.

The method for determining the strength of hardenable material according to the invention can advantageously be used in fabricating a structure from a hardenable material, such as, for example, concrete. In this case, the material is placed in a soft state in a casing, such as, for example, a form. The instant at which the casing can be removed on reaching a predetermined strength can be determined by installing the electrodes in the curing material and determining the strength according to the method according to the invention.

More detailed information on the measurement of dielectric properties is to be found in Hasted, J. B., "Aqueous dielectrics", Chapman and Hall, London, 1973.

It has been found, that in the case of materials which harden as a result of water binding, such as plaster, cement or concrete, the progress of the hardening, or the hydration process, can be satisfactorily reproduced in the change in the dielectric properties described above as a function of time. The change in the dielectric properties as a function of time can be measured as a measure of the degree of hardening at various frequencies of the electric field. In the experiments, good results have been obtained, for example, at frequencies between 10 and 50 MHz. The most reliable are the relative changes with respect to an earlier situation, that is to say each subsequent measurement in time is compared in each case with the measurement during, for example, the initial situation. As a result of measuring the dielectric properties of the hardening material at various instants in time and comparing these measurement results with one another, the method according to the present invention is essentially insensitive to variations in the composition of the hardening material. If the probes with which the measurement of the dielectric properties is carried out remain essentially unchanged in position for the measurements at different instants in time, the measurement is, moreover, essentially insensitive to local differences in composition of the material (consider, for example, gravel in concrete which has not been completely homogeneously mixed). It has, moreover, been found that by measuring the dielectric properties of the hardening material at various instants in time and comparing the measurement results with one another, there is essentially no sensitivity to scale and calibration errors. It has been found that the ratio of the dielectric losses at the instant when the hardenable material is prepared and at a later instant in time correlates well with the degree of hardening of said material. If said material is, for example, concrete, said ratio is a direct indication of the compressive strengths reached by said concrete.

In addition to determining a relative indication of the degree of hardening, the method according to the present invention can also be used to indicate the degree of hardening in an absolute sense. For this purpose, the measured dielectric properties can be compared with dielectric properties determined on test samples having the same or similar composition, or by means of conversion on the basis of, for example, an empirically determined formula or a conversion table.

Figure 2:
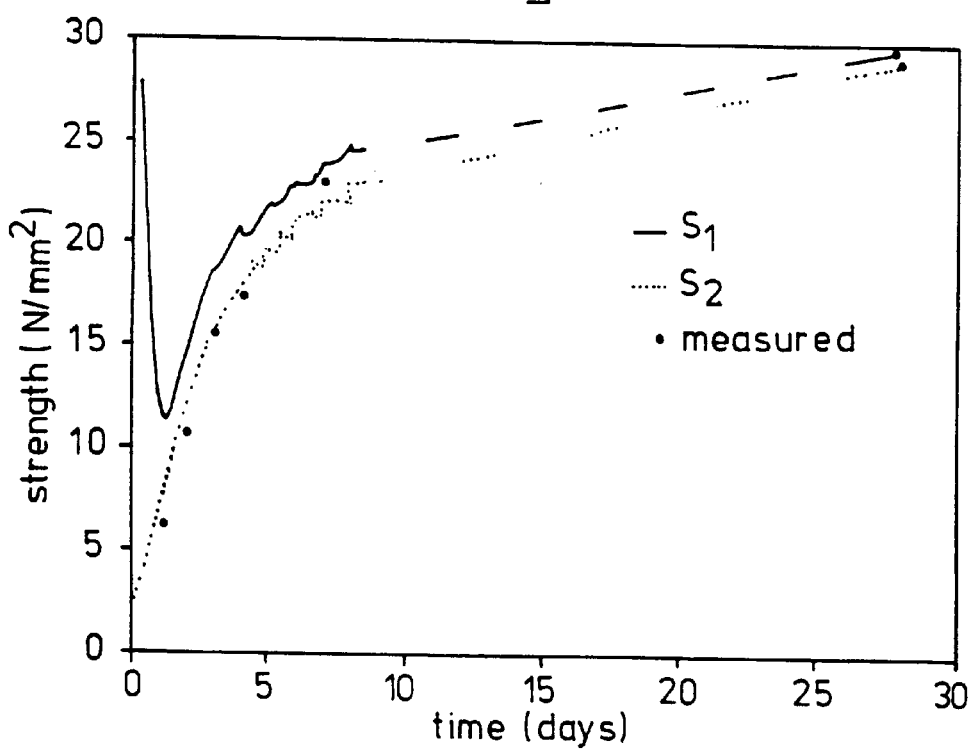
Figure 3:
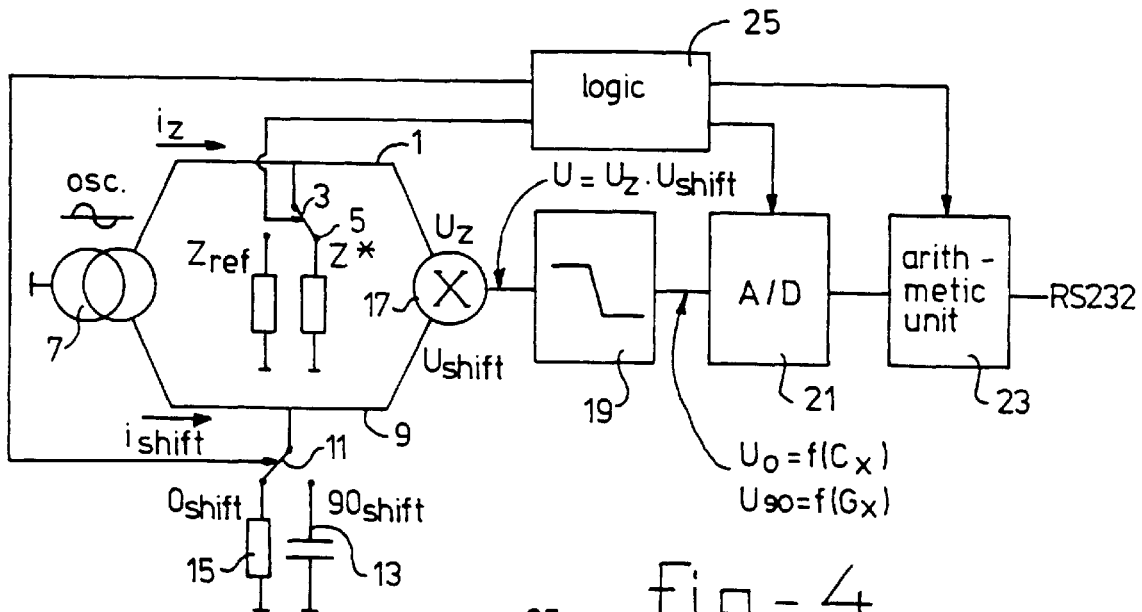
Figure 4:
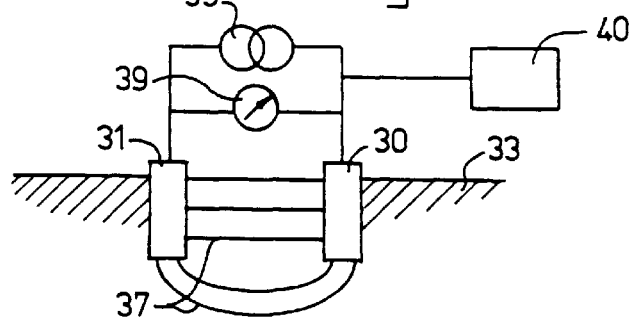
Figure 5:
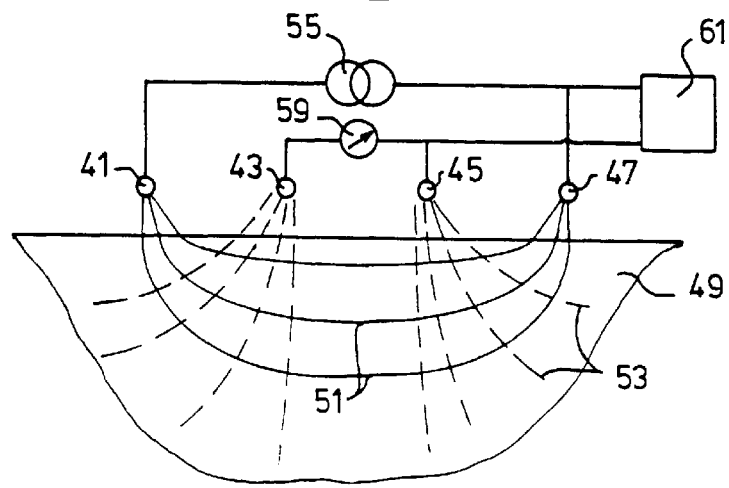

An embodiment of the method and a device according to the present invenion will be explained in greater detail by reference to the accompanying drawing. In the drawing:

FIG. 1 shows the curve of the strength in $N/mm^2$ of curing Portland A concrete and the ratio $\in"(t=0)/\in"(t)$ for a time span of 160 hours, FIG. 2 shows the curve of the calculated compressive strength $S1=53(\in'max/\in'(t)-0.78)$ and $S2=r\in"(t=0)/\in"(t)$ and the measured strength of the curing concrete, FIG. 3 diagrammatically shows the circuit for carrying out the dielectric measurements according to the invention, FIG. 4 shows an arrangement in which the electrodes are situated in the hardenable material, and FIG. 5 shows an arrangement in which four electrodes are situated at a distance from the hardenable material.

To measure the strength of concrete as reproduced graphically in FIG. 1, a test was carried out to determine the complex electrical permittivity of curing Portland A cement having a water/cement ratio of 0.53. The cement was poured into a cube made of expanded polystyrene measuring 15.5 cm ×15.5 cm×15.5 cm. The cubes were then covered with a plastic sheet and sealed with an expanded polystyrene lid. The compressive strength in $N/mm^2$ of the cubes was followed as a function of time. During this procedure the cubes were pressure-loaded until a critical pressure was reached at which the cubes fell apart. Further details of a strength measurement of this type are described in Masted, J. B. "Aqueous Dielectrics".

Two cylindrical electrodes having a length of 3 cm and a diameter of 1 cm were also placed at a mutual spacing of 2 cm in the curing concrete. The complex electrical permittivity was measured at frequencies of 10 MHz, 20 MHz and 30 MHz over a time of 28 days. It was found that the relationship $r \in"(t=0)/\in"(t)$, where r is a scaling factor which depends on the composition of the concrete, very closely follows the strength curve, as measured for the concrete cubes by means of the pressure tests, with the passage of time, as is evident from FIG. 1.

Since the electrical conductivity $G=k\in"\in_0\omega$, the ratio $G(t=0)/G(t)$ will also provide a good measure of the strength of the hardenable material.

In a further test, a concrete sample was taken from a commercial concrete mixing factory which had a water/cement ratio of between 0.45 and 0.55 and for cement types CEM III/B42.5LH HS, CEM I 32.5R, CEM I 42.5R. The concrete was again poured into a cubic form in the same way as described above in connection with FIG. 1. A similar electrode pair was used to measure the electrical permittivity at 20 MHz. The strength of the test cubes was also measured by uniformly pressure-loading them, the pressure at which the cubes collapsed being taken as the strength values.

The measured values for the imaginary part $\in"$ of the complex permittivity were corrected for temperature defects (2%/° C.). A first strength S1 was calculated according to the empirical formula: $S1=53(\in'max/\in'(t)-0.78)$.

A second strength S2 was calculated according to the formula: $S2=r\in"(t=0)/\in"(t)$.

Here $\in'max$ is the maximum value of the real part of permittivity which is found as a function of the time elapsed t. The value r is a scaling factor which depends on the composition of the concrete. As is evident from FIG. 2, the force Per unit area S1 alone is a good reflection of the strength after $\in'max$ has occurred, while the force value per unit area S2 is valid from instant in time t=0.

As is evident from FIG. 2, there is a good fit between the calculated forces per unit area S1 and S2 and the measured strength of the concrete samples. The calculated forces S1 and S2 are relatively insensitive to temperature and composition and factors such as the electrode dimensions and any stones between the electrodes. The calculated value S1 was universally applicable, while a scaling factor r had to be determined for S2 to obtain a better fit with the measured force S. The maximum difference between the measured force S and S1 was pproximately 6 N $mm^2$, which is close to the accuracy of standard methods of determining the strength.

The scaling factor r can advantageously be determined by measuring the force S1 at $\in'max$, which is approximately 10.5 newtons/$mm^2$ in FIG. 2. By then postulating that $10.5=r\in"(t=0)/\in"(t)$, the factor r can be determined.

FIG. 3 diagrammatically shows the measurement arrangement for determining the real part $\in'(t)$ and the imaginary part $\in"(t)$ of the complex permittivity. The electrode configuration with the hardenable material in between as dielectric is represented as a complex impedance $Z^*$. Via a supply line 1, an alternating current is supplied via a switch 3 to a supply terminal 5 of the impedance $Z^*$, which is formed by two or more electrodes with hardening material in between as dielectric. The alternating current source 7 is formed by a crystal oscillator which generates a sinusoidal current having an adjustable oscillator frequency of between 1 MHz and 100 MHz. The output signal of the oscillator 7 is supplied to a switch 11 via a branching line 9. The switch 11 can be selectively connected to a phase-rotating component such as a capacitor 13 or a non-phase-rotating component such as a resistor 15. The supply terminal 5 of the electrode configuration and the supply terminal of the capacitor 13 or the resistor 15 are connected to a multiplier 17, the voltages formed across the electrode configuration $Z^*$ and the component 13 or 15, $U_z$ and $U_{shift}$ respectively, being multiplied by one another. The product $U_z \cdot U_{shift}$ is supplied to a low-pass filter 19. The signal at the output of the low-pass filter 19 is converted in an analogue/digital converter 21, whose output is connected to the input of an arithmetic unit 23. In the arithmetic unit 23, the real part $\in'(t)$ and the imaginary part $\in"(t)$ of the complex permittivity are determined. The relationships $53.(\in'max/\in'(t)-0.78)$ and/or $\in"(t=0)/\in"(t)$ are then calculated in the arithmetic unit 23. By means of a time control unit 25, the switches 3, 11, the analogue/digital converter 21 and the arithmetic unit 23 are triggered to make a measurement at predetermined time intervals, for example every hour over a period of, for example, 30 days.

The measurement of the impedance $Z^*$ of the electrode configuration is based on synchronous detection. The sinusoidal voltage having a frequency $\omega$ which is chosen between 1 MHz and 100 MHz is fed to the multiplier 17. The phase of the current which is fed via the branching line 9 to the multiplier 17 can be rotated through 0° or 90° in phase by positioning the switch 11. The voltage $U_z$, which is developed on the supply terminal of the phase-rotating component 13 or the non-phase-rotating component 15 is fed to the other supply terminal of the multiplier 17. The output voltage $U=U_z U_{shift}$ of the multipliers has a frequency component having a frequency $2\omega$ and a direct-voltage component. The low-pass filter 19 removes the alternating-voltage component having a frequency $2\omega$. If the switch 11 is connected to the resistor 9, no phase rotation takes place and the direct voltage is a measure of the capacitance of the impedance $Z^*$. If the switch 11 is connected to the capacitor 13, the voltage on the output terminal thereof is rotated through 90°. This voltage is a measure of the conductivity G of the impedance $Z^*$. Since $Z^*=1/(G=j\omega C)=1/(j\omega(\in'-j\in")\in_0 k)$, $\in'$ and $\in"$ can be calculated here in the arithmetic unit 23.

The measurements are repeated for a reference impedance $Z_{ref}$ to calibrate the sensor automatically. Preferably, the circuit in FIG. 3 is embodied as an integrated circuit in the form of an ASIC.

FIG. 4 diagrammatically shows an electrode configuration, in which two electrodes 30, 31 are installed in a layer of hardenable material 33. The electrodes are connected to an alternating-current source 35. The current tracks between the electrodes 30, 31 are indicated diagrammatically by 37. The voltage generated by the current flowing between the electrodes 30, 31 is measured across the supply terminals of said electrodes with the aid of a voltmeter 39. The output signal of the voltmeter 39 is fed to a signal processing unit 40, which comprises, for example, a multiplier 17, a low-pass filter 19, an analogue/digital converter 21, an arithmetic unit 23 and a time control unit 25, as shown in FIG. 3.

FIG. 5 shows an alternative arrangement, in which four electrodes 41, 43, 45 and 47 are situated above a base 49. The current paths are indicated by 51 and the equipotential lines by 53. With the aid of a current source 55, a current is fed along current paths 51 through the material 49 from an electrode 41 to an electrode 47. The potential formed in the material 49 is measured with the aid of the electrodes 43, 45. The output of the voltmeter 59 is connected to a signal processing unit 61, which may comprise the same components as the signal processing unit 40 of FIG. 4. The advantage of the arrangement according to FIG. 5 is that no electrodes have to be installed in the material 49 and that the hardening process of the latter can be observed at a distance without damaging the material.

We claim:

1. A method for determining the degree of hardening of a hardenable material comprising the step of:
    determining the complex electrical permittivity of the hardenable material at various instants in time by determining both:
    i) the ratio $\in''(t=0)/\in''(t)$ of the imaginary part, $\in''(t)$, of the complex electrical permittivity $\in'(t)-j\in''(t)$ at a reference instant in time t=0 and at an instant in time t, and
    ii) the ratio $\in'max/\in'(t)$ of the maximum value of the real part of the complex electrical permittivity $\in'max$ over the time interval t=0 to t and the real part of the complex electrical permittivity $\in'(t)$ at the instant in time t, as a measure of the strength of the hardenable material at an instant in time t,
    wherein the measurements are taken at frequencies between 1 MHz and 17 GHZ.

2. Method according to claim 1, wherein said step of determining the ratio $\in''(t=0)/\in''(t)$ comprises the further steps of determining the imaginary part of the electrical permittivity $\in''(t)$ by placing at least two electrodes in or near the hardenable material, applying an alternating current across the electrodes, measuring the alternating voltage across the electrodes, determining the complex impedance $$Z^* = \frac{1}{G + j\omega C},$$

where G is the conductivity of the hardenable material in S/m and C is the capacitance in F, and determining $\in''(t)$ via the relationship:

$G(t)=k\in''(t)\in_0\cdot\omega.$

3. Method according to claim 1, wherein said step of determining the ratio $\in''(t=0)/\in''(t)$ comprises the further steps of determining the imaginary part of the electrical permittivity $\in''(t)$ by placing at least two electrodes in or near the hardenable material, applying an alternating current across the electrodes, measuring the alternating voltage across the electrodes, determining the complex impedance $$Z^* = \frac{1}{G + j\omega C},$$

where G is the conductivity of the hardenable material in S/m and C is the capacitance in F, and determining $\in''(t)$ via the relationship: $C(t)=k\in'(t)\in_0$, where k is a constant.

4. Method according to claim 1, wherein the time during which the hardness is determined is between 1 day and 100 days.

5. Method according to claim 1, wherein the time during which the hardness is determined is between 1 day and 30 days.

6. Method according to claim 1, wherein said step of determining the ratio $\in''(t=0)/\in''(t)$ comprises the further step of determining the imaginary part, $\in''(t)$, of the complex electrical permittivity $\in'(t)-j\in''(t)$ at a frequency between 15 and 50 MHz.

7. Method according to claim 1, wherein said step of determining the ratio $\in''(t=0)/\in''(t)$ comprises the further step, prior to the measurement of $\in''(t)$, carrying out a calibration to determine a scaling factor, r, which depends on the composition of the hardenable material and applying the ratio $r\cdot\in''(t=0)/\in''(t)$ to determine a measure of the strength of the material.

8. Method according to claim 7, wherein said calibration step determines the strength at the maximum value of the real part of the permittivity, $\in'max$, and wherein the ratio $\in''(t=0)/\in''(t)$ is determined for the instant in time at which $\in'max$ is found, after which the scaling factor r is determined, the strength being determined for later instants in time by $r\cdot\in''(t=0)/\in''(t)$.

9. Method according to claim 1, wherein the hardenable material is a material which hardens as a result of water binding.

10. Method according to claim 9, wherein the material is one of concrete, plaster, and cement.

11. Device for carrying out the method according to claim 1, wherein the device comprises:
    at least two electrodes which can be connected to the hardenable material,
    an alternating-current source for supplying an alternating current to a supply terminal of the electrodes via a supply line at a frequency between 1 Mhz and 17 Ghz,
    a switching device for selective connection of the alternating-current source via a branching line to a supply terminal of a phase-rotating component or a non-phase-rotating component,
    a multiplier whose input is connected to the supply terminal of the electrodes and to the switching device,
    a low-pass filter whose input is connected to the output of the multiplier,
    an arithmetic unit connected to the low-pass filter for determining the imaginary part $\in''(t)$ and the real part $\in'(t)$ of the complex electrical permittivity from one of the conductivity G(t) and the capacitance C(t) of the hardenable material according to the equations $G(t)=k\in''(t)\cdot\in_0\cdot\omega$ and $C(t)=k\in'(t)\cdot\in_0$ respectively, arranged to determine the ratio's $\in''(t=0)/\in''(t)$ and $\in'max/\in'(t)$ respectively where k is a constant and t is the time, and
    a time control unit for reading-in signals at the output of the filter at a number of consecutive instants in time.

12. The device of claim 11, wherein the device comprises:

an alternating-current source for supplying an alternating current to a supply terminal of the electrodes via a supply line at a frequency between 15 Mhz and 50 Mhz.

13. The device of claim 11, wherein the device comprises:

wherein said arithmetic unit is designed and constructed to carrying out a calibration to determine a scaling factor, r, which depends on the composition of the hardenable material and applying the ratio $r \cdot \in''(t=0)/\in''(t)$ to determine a measure of the strength of the material, and wherein said calibration determines the strength at the maximum value of the real part of the permittivity, $\in'max$, and wherein said arithmetic unit operates to determine the ratio $\in''(t=0)/\in''(t)$ for the instant in time at which $\in'max$ is found and after which the scaling factor r is determined, the strength being determined for later instants in time by $r \cdot \in''(t=0)/\in''(t)$.

14. Method of claim 1 for fabricating a structure made of hardenable material, comprising the further steps during manufacturing:

placing the material in a soft state in a casing, determining the strength, and removing the casing when a predetermined strength is reached.

* * * * *